United States Patent [19]
Gosserez

[11] Patent Number: 4,902,294
[45] Date of Patent: Feb. 20, 1990

[54] IMPLANTABLE MAMMARY PROSTHESIS ADAPTED TO COMBAT THE FORMATION OF A RETRACTILE SHELL

[76] Inventor: Olivier Gosserez, Quartier Didier Allée de la Louisiane, 97200 Fort de France, Martinique, France

[21] Appl. No.: 124,856

[22] Filed: Nov. 30, 1987

[30] Foreign Application Priority Data

Dec. 3, 1986 [FR] France ............................ 86 16893

[51] Int. Cl.⁴ ................................................ A61F 2/12
[52] U.S. Cl. ................................................ 623/8
[58] Field of Search ............... 623/7, 8, 11; 128/1 R; 604/8

[56] References Cited

U.S. PATENT DOCUMENTS

| | | | |
|---|---|---|---|
| 3,452,757 | 7/1969 | Ames | 604/8 |
| 4,125,117 | 11/1978 | Lee | 623/7 |
| 4,195,639 | 4/1980 | Lee | 128/481 |
| 4,264,990 | 5/1981 | Hamas | 623/8 |
| 4,574,780 | 3/1986 | Manders | 623/8 |
| 4,634,443 | 1/1987 | Haber | 128/1 R |

FOREIGN PATENT DOCUMENTS 0005275 11/1979 European Pat. Off.

Primary Examiner—Richard J. Apley
Assistant Examiner—David J. Isabella
Attorney, Agent, or Firm—Young & Thompson

[57] ABSTRACT

An implantable mammary prosthesis designed to combat the formation around it of a retractile shell in reaction to a foreign body comprises a pocket with a front wall that can be inflated to a dome shape by injecting a physiological serum through a valve. The pocket is attached to a back wall to a sheet which is generally oval-shaped symmetrically relative to a major axis. The pocket is placed on the sheet so as to be spaced from the edges thereof on all sides by a distance of at least one fifth the radius of the pocket. The inside edge of the sheet, meaning that to be placed nearest the sternum, is narrower than the outside edge. The sheet is designed to impede retraction of the fibrous shell by creating a reflection line which breaks the continuity of curvature of the shell, so that the latter loses its retractile potential.

16 Claims, 1 Drawing Sheet

IMPLANTABLE MAMMARY PROSTHESIS ADAPTED TO COMBAT THE FORMATION OF A RETRACTILE SHELL

BACKGROUND OF THE INVENTION

1. Field of the Invention

The invention relates to an implantable mammary prosthesis adapted to combat the formation around it of a retractile shell in reaction to a foreign body, comprising a flexible pocket having a generally circular base and made from a biocompatible film material filled out to a dome shape by filling it with an appropriate fluid.

2. Description of the prior art

Broadly speaking, conventional implantable mammary prostheses are divided into two categories: the so-called pre-filled prostheses which contain a silicone gel to maintain the dome shape of the pocket even before implantation, and the so-called inflatable prostheses which are formed to shape in situ by injecting a physiologically acceptable liquid of the physiological serum type.

Nevertheless, whichever category of prosthesis is used, its implantation leads to a foreign body reaction in the organism, this reaction manifesting itself in the formation of a living membrane made up of, among other things, fibroblast collagen and myofibroblasts which completely surround the prosthesis and isolate it from the organism.

In 70 to 80% of cases this membrane remains thin and flexible and does not lead to any modification of the shape or consistency of the fitted prosthesis.

In 20 to 30% of cases, however, over a period of months or years following implantation the membrane thickens and retracts to form a shell approximating the shape of a sphere to a greater or lesser degree. This geometrical shape is, of course, that for which the surface area to volume ratio is minimal. It goes without saying that the formation of a retractile shell of this kind is the opposite of the esthetic result looked for.

At the time of writing the problem raised by the risk of a retractile fibrous shell of this kind forming has not found a satisfactory solution. All attempted solutions relating to the membrane, to the content of the prosthesis, to the nature of the surface of the pocket and to the anatomical positioning of the prosthesis have proved unsatisfactory.

SUMMARY OF THE INVENTION

The invention consists in an implantable mammary prosthesis adapted to combat the formation around it of a retractile shell in reaction to a foreign body, comprising a flexible pocket having a generally circular base and made from a biocompatible film material filled out to a dome shape by filling it with an appropriate fluid and a flexible sheet of biocompatible film material from which said pocket projects and which has a peripheral edge surrounding said pocket, the distance between said edge and said pocket being substantially at least one fifth the radius of said pocket.

The inventor has noticed that in general surgery the introduction of a foreign material into the organism induces consistently a foreign body reaction but that the newly formed tissue does not show any comparable tendency to retraction. In surgical treatment of major hernias, in particular, large sheets or plates of woven material (dacron) or metal are implanted and induce non-retractile fibrous reactions.

The inventor was therefore led to reconsider the shape of mammary prostheses, which are approximately the same size in all three dimensions, and to design a prosthesis which comprises a sheet part, very thin in relation to its length and its width, which borders the pocket on all sides, so protecting it from retraction.

The surface area of the sheet is preferably at least twice that of the base of the pocket.

The periphery of the sheet preferably is in the shape of a closed curve without any sharp corners or points of inflection.

These conditions are directed to optimizing the defectiveness of the sheet.

Other characteristics and the advantages of the invention will emerge from the following description of one embodiment thereof, given with reference to the appended drawings.

DESCRIPTION OF THE PREFERRED EMBODIMENT

In the chosen embodiment shown in the figures, the mammary prosthesis comprises a pocket 1 applied through its posterior surface 11 to a sheet 2, this posterior surface 11 adhering to the sheet over all of its area.

It should be made clear at once that the various parts of the prosthesis are qualified with reference to their position when fitted to the patient. Thus the posterior surface 11 of the pocket 1 will be that closest to the thorax.

The pocket 1 is of conventional construction in itself and thus may be of either of the two types of prosthesis that currently exist:

either an empty pocket, virtually empty before implantation, which is inflated with a physiological liquid through a valve 13 (this is the situation shown in the figures);

or a pre-filled and hermetically sealed pocket containing a silicone gel.

The prosthesis as a whole is made from a biocompatible material, for which there are numerous options available depending on the implantation site (on top of or behind the pectoral muscles).

Figure 1:
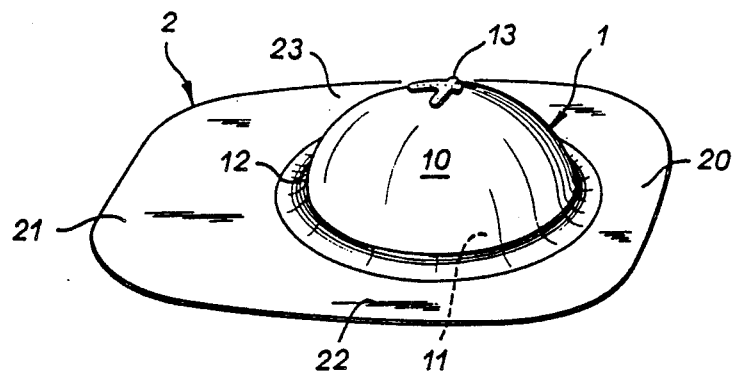
FIG. 1 is a perspective view of a prosthesis in accordance with the invention.
Figure 2:
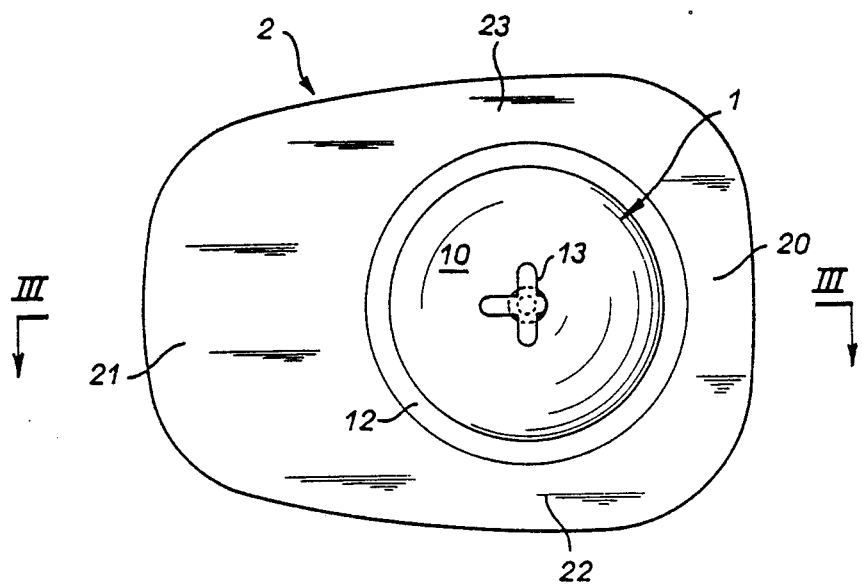
FIG. 2 is a plan view of the prosthesis shown in FIG. 1.
Figure 3:
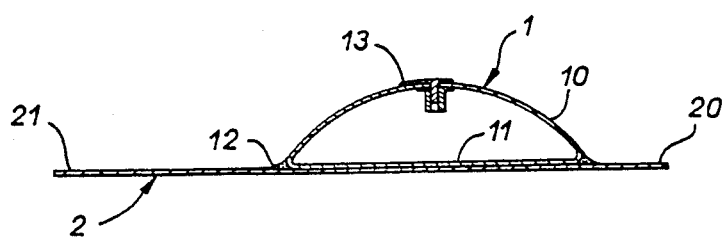
FIG. 3 is a cross-section on the line III—III in FIG. 2.

The sheet 2 is made from a medical grade biocompatible film material and has a nearly oval shape symmetrical relative to its major axis which coincides with the section line III—III in FIG. 2. The pocket 1 is centered on the major axis of the sheet 2 and nearer the internal end of this major axis of the sheet 2 and nearer the internal end of this major axis that its external end. By internal end is meant that nearer the sternum after implantation.

The periphery of the pocket 1 is spaced from the edge of the sheet all the way round, so defining an inside edge 20, an outside edge 21, a lower edge 22 and an upper edge 23 of the sheet. The sheet has its maximal width between the lower edge 22 and the upper edge 23, substantially in line with the center of the pocket 1.

The fixing of the pocket 1 to the sheet is reinforced at the periphery of the posterior wall 11 by a bead 12. Continuity of the surface prevents any anchoring of the prosthesis.

As already explained in the preamble, the edges 20 through 23 are designed to keep away from the base of the pocket 1 the periphery of the fibrous membrane that will form around the prosthesis by virtue of foreign body reaction. It will be immediately understood that the effectiveness of the edges 20 through 23 is conditioned by their width, given the anatomical possibilities available for placing the prosthesis.

In the example shown, the inside edge 20, lower edge 22 and upper edge 23 have a minimal width close to one half the radius of the periphery of the pocket (excluding the bead 12, of course), whereas the outer edge 21 has a width of approximately 1.4 times the radius of the pocket 1.

The ratio of the distances along the major axis of the sheet 2 from the center of the pocket to the peripheries of the internal edge 20 and the external edge 21, respectively, is approximately 0.67:1.

This ratio allows for the anatomical constraints of the receiving site, limiting the possible extent of the sheet because of the necessity to preserve the adherence of the skin in the region of the sternum.

It will have been understood that the description has been given with reference to a right breast prosthesis but that, by virtue of the symmetry of the edges 22 and 23, it is sufficient to rotate the posthesis in the plane of FIG. 2 for it to be usable as a left breast, the lower edge becoming the upper edge and vice versa.

The example described here is considered to be the optimum for achieving a compromise between the effectiveness of protection against the formation of fibrous shells and anatomical compatibility with the typical patient. It will be understood, however, that it may be necessary to depart from the example as described for anatomical or other reasons. Experience indicates that the distance between the pocket 1 and the periphery of the sheet 2 should not be less than 1/5 of The radius of the pocket 1. Also, given that the total surface area of the sheet is an important parameter in combatting the appearance of fibrous shells, it is highly desirable for the surface area of the sheet to be at least twice that of the pocket 1.

Also, it has been stated that the periphery of the sheet should be a closed curve comprising neither sharp corners nor points of inflection. The presence of points of inflection produces re-entrant parts of the periphery and consequently a reduction in the useful surface area of the sheet relative to its total surface area.

It is to be understood that the invention is not limited to the examples described but rather encompasses any variant execution thereof within the scope of the appended claims.

Thus the pocket 1 could be molded in one piece with the sheet 2, rather than attached to it.

I claim:

1. Implantable mammary prosthesis adapted to combat the formation around it of a retractile shell in reaction to a foreign body, comprising a flexible pocket having a generally circular base, made from a surgical grade biocompatible film material and being dome shaped when filled with an appropriate fluid, and a substantially flat flexible sheet of surgical grade biocompatible film material, said circular base being integral with said flexible sheet, a base perimeter being defined on the flexible sheet at the perimeter of the circular base; wherein the improvement comprises a flexible peripheral flange formed by the flexible sheet extending continuously circumferentially around the base perimeter and extending outwardly therefrom a distance equal to at least one fifth the radius of said circular base, whereby said flexible periphery flange prevents fibrous membrane from causing capsular contraction about said mammary prosthesis.

2. Prosthesis according to claim 1, wherein the surface area of said sheet is at least twice that of said base of said pocket.

3. Prosthesis according to claim 1, wherein the periphery of said sheet has the shape of a closed curve free from sharp corners and free from points of inflection.

4. Prosthesis according to claim 3, wherein said sheet is of generally oval shape with major and minor axes and said base of said pocket has its center situated on said major axis, closer to one end thereof than the other.

5. Prosthesis according to claim 4, wherein said oval sheet has a maximal width along a line perpendicular to said major axis intersecting the same substantially at the center of said pocket base.

6. Prosthesis according to claim 1, wherein said biocompatible film material is medical grade silicone.

7. Prosthesis according to claim 1, further comprising means for inflating said flexible pocket in situ by injecting a physiologically acceptable liquid.

8. Prosthesis according to claim 7, wherein said pocket comprises a filling valve at the summit of its dome shape.

9. Prosthesis according to claim 1, wherein said flexible pocket is pre-filled with a silicone gel and hermetically sealed.

10. Implantable mammary prosthesis adapted to combat the formation around it of a retractile shell in reaction to a foreign body, said prosthesis having a generally circular base, said prosthesis being made from a biocompatible film material and being dome shaped when filled with an appropriate fluid, and a flexible sheet of biocompatible film material, said circular base being integral with said flexible sheet, a base perimeter being defined on the flexible sheet at the perimeter of the circular base; wherein the improvement comprises a flexible peripheral flange formed by the flexible sheet extending continuously circumferentially around the base perimeter and extending outwardly therefrom a distance equal to at least one fifth the radius of said circular base, the periphery of said flexible sheet having a shape of a closed curve free from sharp corners and free from points of inflection, said closed curve being of generally oval shape with major and minor axes, and said base of said pocket having its center situated on the major axis, the ratio of the distances from the center of said pocket base to respective ends of said major axis being at most 0.7:1.

11. Prosthesis according to claim 10, wherein the surface area of said sheet is at least twice that of said base of said pocket.

12. Prosthesis according to claim 10, wherein said oval sheet has a maximum width along a line perpendicular to said major axis, intersecting the same substantially at the center of said pocket base.

13. Prosthesis according to claim 10, wherein said biocompatible film material is medical grade silicone.

14. Prosthesis according to claim 10, further comprising means for inflating said flexible pocket in situ by injecting a physiologically acceptable liquid.

15. Prosthesis according to claim 14, wherein said pocket comprises a filling valve at the summit of its dome shape.

16. Prosthesis according to claim 10, wherein said pocket is prefilled with a silicone gel and hermetically sealed.

* * * * *